(12) United States Patent
Fukutani

(10) Patent No.: US 9,594,060 B2
(45) Date of Patent: Mar. 14, 2017

(54) OBJECT INFORMATION ACQUISITION APPARATUS, OBJECT INFORMATION ACQUISITION METHOD AND PROGRAM

(71) Applicant: CANON KABUSHIKI KAISHA, Tokyo (JP)

(72) Inventor: Kazuhiko Fukutani, Kyoto (JP)

(73) Assignee: Canon Kabushiki Kaisha, Tokyo (JP)

(*) Notice: Subject to any disclaimer, the term of this patent is extended or adjusted under 35 U.S.C. 154(b) by 218 days.

(21) Appl. No.: 14/390,319

(22) PCT Filed: Apr. 3, 2013

(86) PCT No.: PCT/JP2013/060767
§ 371 (c)(1),
(2) Date: Oct. 2, 2014

(87) PCT Pub. No.: WO2013/154116
PCT Pub. Date: Oct. 17, 2013

(65) Prior Publication Data
US 2015/0049581 A1 Feb. 19, 2015

(30) Foreign Application Priority Data
Apr. 12, 2012 (JP) .................................. 2012-091280

(51) Int. Cl.
*G01N 29/06* (2006.01)
*A61B 5/00* (2006.01)
*G01N 29/24* (2006.01)

(52) U.S. Cl.
CPC ....... *G01N 29/0654* (2013.01); *A61B 5/0095* (2013.01); *A61B 5/7207* (2013.01); *G01N 29/2418* (2013.01); *G01N 2223/40* (2013.01)

(58) Field of Classification Search
CPC ... A61B 5/7207; A61B 5/0095; G01N 29/2418; G01N 29/0654; G01N 2223/40
See application file for complete search history.

(56) References Cited

U.S. PATENT DOCUMENTS

| | | | |
|---|---|---|---|
| 8,203,911 B2* | 6/2012 | Kremeyer | G01N 21/1702 367/128 |
| 2009/0103083 A1* | 4/2009 | Kremeyer | G01N 21/1702 356/317 |

(Continued)

FOREIGN PATENT DOCUMENTS

| | | | |
|---|---|---|---|
| EP | 2345364 A1 | 7/2011 | |
| JP | WO 2013154116 A1 * | 10/2013 | ........... A61B 5/7207 |

(Continued)

OTHER PUBLICATIONS

"Photoacoustic imaging in biomedicine", M.Xu,L.V.Wang, Review of Scientific Insturument, 77, 041101, 2006.

*Primary Examiner* — Daniel Pihulic
(74) *Attorney, Agent, or Firm* — Canon USA, Inc. I.P. Division

(57) ABSTRACT

An object information acquisition apparatus includes: a plurality of acoustic wave detecting elements configured to detect an photoacoustic wave generated when an object is irradiated with light and output time-series detection signals; a member disposed outside the object; and a signal processing unit configured to acquire optical property information inside the object by performing image reconstruction through iterative reconstruction method in accordance with the time-series detection signals and an operand for which a response of the photoacoustic wave deriving from the member has been considered.

20 Claims, 9 Drawing Sheets

(56) References Cited

U.S. PATENT DOCUMENTS

| | | | |
|---|---|---|---|
| 2010/0053618 A1* | 3/2010 | Nakajima | A61B 5/0059 356/432 |
| 2010/0208965 A1* | 8/2010 | Jiang | A61B 5/0073 382/131 |
| 2011/0178739 A1* | 7/2011 | Tanji | A61B 5/0059 702/56 |
| 2011/0232385 A1 | 9/2011 | Nanaumi | |
| 2011/0257530 A1* | 10/2011 | Tokita | A61B 5/0091 600/443 |
| 2012/0133941 A1* | 5/2012 | Nakajima | A61B 5/0059 356/432 |
| 2012/0190963 A1* | 7/2012 | Fukutani | A61B 5/0091 600/407 |
| 2013/0114859 A1* | 5/2013 | Wanda | A61B 5/0095 382/103 |
| 2015/0049581 A1* | 2/2015 | Fukutani | A61B 5/7207 367/7 |

FOREIGN PATENT DOCUMENTS

| | | |
|---|---|---|
| WO | 2009/011934 A1 | 1/2009 |
| WO | 2011/040003 A1 | 4/2011 |
| WO | 2012/011242 A1 | 1/2012 |

\* cited by examiner

OBJECT INFORMATION ACQUISITION APPARATUS, OBJECT INFORMATION ACQUISITION METHOD AND PROGRAM

TECHNICAL FIELD

The present invention relates to an object information acquisition apparatus configured to acquire optical property information in accordance with a detection signal obtained upon detection of a photoacoustic wave generated when an object is irradiated with light.

BACKGROUND ART

In the medical field, an optical imaging device configured to image information inside an object, such as a living body, acquired upon irradiation of the object with light from a light source, such as a laser, has been intensively studied.

One of such optical imaging techniques is photoacoustic imaging (PAI). In the photoacoustic imaging, an acoustic wave detector (e.g., a probe) detects a photoacoustic wave (which is typically an ultrasonic wave) generated upon irradiation of an object with pulsed light which is emitted from a light source. By analyzing the detection signal mathematically, it is possible to obtain optical property value distribution within the object. The optical property value distribution may include initial acoustic pressure distribution, optical energy absorption density distribution and absorption coefficient distribution. Such information may be used for a quantitative measurement of a special material in the object, such as oxygen saturation in the blood.

Recently, pre-clinical studies to image blood vessel figures of small animals using the photoacoustic imaging and clinical studies to apply this principle to, for example, diagnosis of the breast cancer have been intensively continued ("Photoacoustic imaging in biomedicine" M. Xu, L. V. Wang, REVIEW OF SCIENTIFIC INSTRUMENT, 77, 041101, 2006).

However, in the optical property value distribution obtained by the photoacoustic imaging, decreases in resolution and in quantitativity have occurred due to various factors. Therefore, in the photoacoustic imaging, further improvement in resolution and in quantitativity has been needed.

SUMMARY OF INVENTION

The present invention provides an object information acquisition apparatus and an object information acquisition method capable of reducing, in photoacoustic imaging, decreases in resolution and in quantitativity.

An object information acquisition apparatus, including: a plurality of acoustic wave detecting elements configured to detect an photoacoustic wave generated when an object is irradiated with light and output time-series detection signals; a member disposed outside the object; and a signal processing unit configured to acquire optical property information inside the object by performing image reconstruction through iterative reconstruction method in accordance with the time-series detection signals and an operand for which a response of the photoacoustic wave deriving from the member has been considered.

Further features of the present invention will become apparent from the following description of exemplary embodiments with reference to the attached drawings.

DESCRIPTION OF EMBODIMENT

Figure 1:
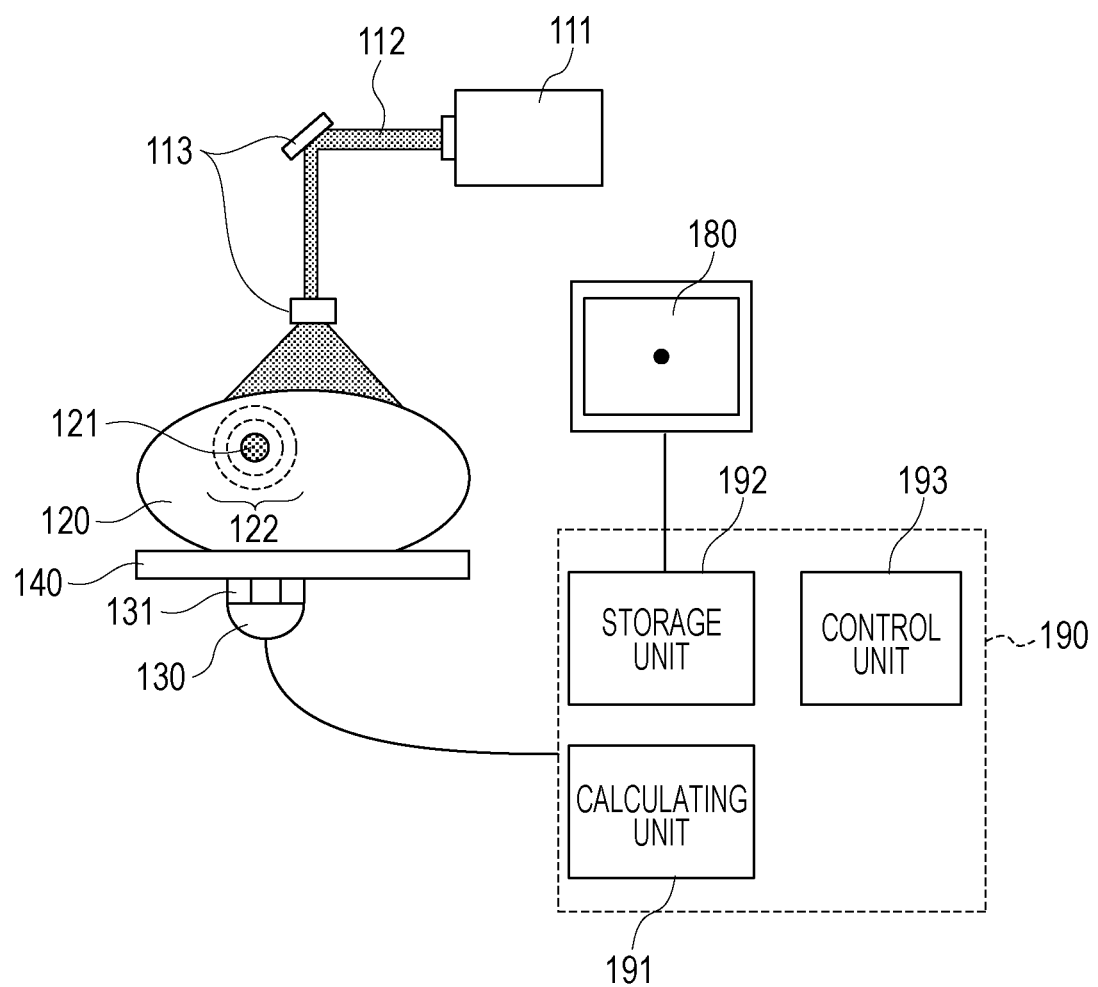
FIG. 1 is a diagram schematically illustrating an object information acquisition apparatus according to the present embodiment.

Hereinafter, the present invention will be described in more detail with reference to the drawings. The same component will be denoted by the same reference numeral and description thereof will be omitted.

Basic Configuration

First, a basic configuration of an object information acquisition apparatus according to the present embodiment will be described with reference to FIG. 1. The object information acquisition apparatus of the present embodiment is configured to acquire optical property information inside an object. The optical property information according to the present embodiment includes the initial acoustic pressure of a photoacoustic wave generated by a photoacoustic effect, the optical energy absorption density deriving from the initial acoustic pressure, an absorption coefficient, and the concentration of a substance which constitutes a tissue. Here, the concentration of a substance is, for example, oxygen saturation, oxyhemoglobin concentration, deoxyhemoglobin concentration and the total hemoglobin concentration. The total hemoglobin concentration is the sum of oxyhemoglobin concentration and deoxyhemoglobin concentration. The optical property information in the present embodiment is not necessarily numerical data but may be distribution information at each position in the object. That is, distribution information, including absorption coefficient distribution and oxygen saturation distribution, may be used as the optical property information.

Figure 2:
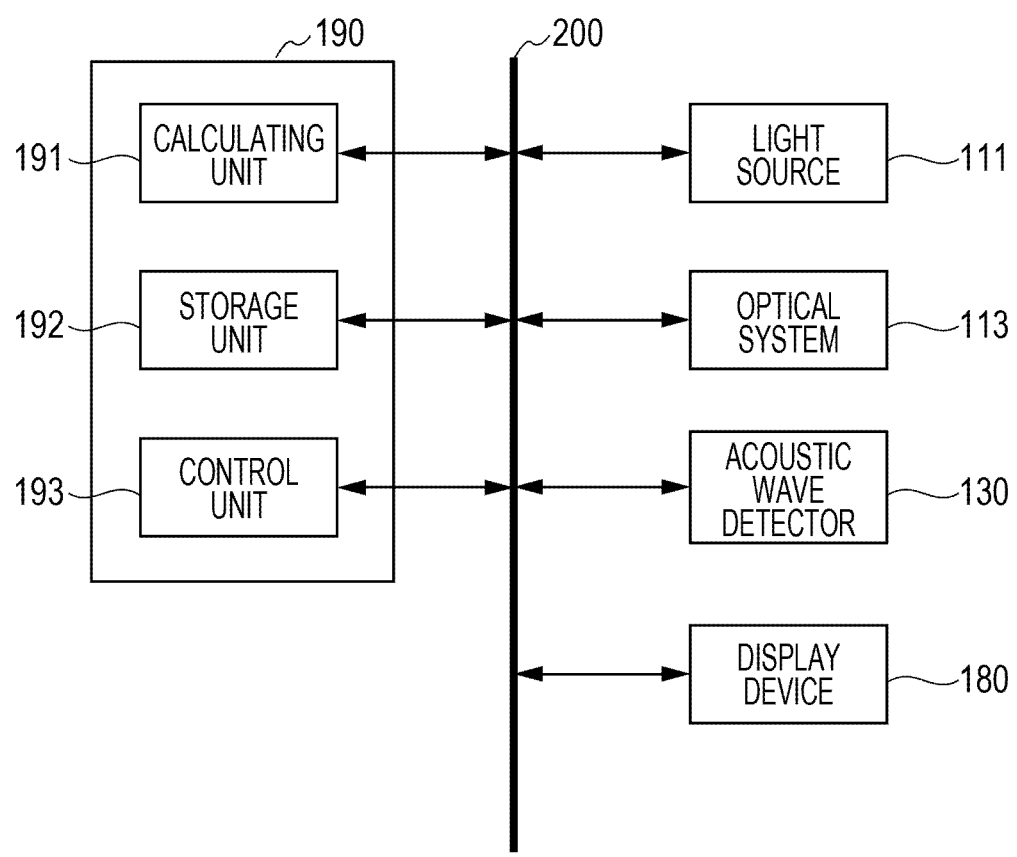
FIG. 2 is a diagram illustrating a signal processing device and a peripheral configuration thereof according to the present embodiment.

The object information acquisition apparatus of the present embodiment includes, as a basic hardware structure, a light source 111, a holding member 140 configured to hold an object 120, an acoustic wave detector 130 including a plurality of acoustic wave detecting elements 131, and a signal processing device 190. Here, in the present embodiment, the holding member 140 corresponds to a member provided between the object 120 and the acoustic wave detecting elements 131. FIG. 2 is a schematic diagram illustrating details of the signal processing device 190 and a peripheral configuration of the signal processing device 190. The signal processing device 190 as a signal processing device includes a calculating unit 191, a storage unit 192 and a control unit 193. The control unit 193 controls, via a bus 200, an operation of each component of the object information acquisition apparatus. In the storage unit 192, a program in which an object information acquisition method described later is written is stored. The control unit 193 reads the program from the storage unit 192 and makes the object information acquisition apparatus execute the object information acquisition method.

In the present embodiment, object information is acquired in the following manner.

Pulsed light 112 emitted from the light source 111 is guided by an optical system 113 which consists of, for example, a lens, a mirror, optical fiber and a diffuser plate while being formed into a desired light distribution shape. The pulsed light 112 illuminates the object 120. When a part of the energy of light which has propagated inside the object 120 is absorbed by an optical absorber (i.e., an acoustic source) 121, such as a blood vessel, a photoacoustic wave 122 is generated due to thermal expansion of the optical absorber 121.

The photoacoustic wave 122 causes, for example, reflection, refraction and absorption, in the holding member 140 in accordance with the acoustic characteristics of the holding member 140. A plurality of acoustic wave detecting elements 131 detect the photoacoustic wave 122 which has been thus affected by the holding member 140 and output time-series detection signals. The calculating unit 191 performs, for example, an amplification process and a digital conversion process to the detection signals detected by the acoustic wave detecting elements 131. The optical property information is acquired by the calculating unit 191 performing a predetermined process using the detection signals. The object information is then converted into image data by the calculating unit 191 and is displayed on a display device 180.

In the photoacoustic imaging, decreases in resolution and in quantitativity are caused by various factors. The factors may include reflection, refraction and absorption of a photoacoustic wave generated inside the object in a member provided outside the object.

Here, the member provided outside the object may include a member provided between the object and the acoustic wave detecting elements and a member provided in the circumference of the object. The member provided between the object and the acoustic wave detecting elements may include a holding member configured to hold the object, an acoustic matching material for acoustic impedance matching between the object and the acoustic wave detecting elements, a member configured to hold the acoustic matching material, and a protective layer of the acoustic wave detector. The member provided in the circumference of the object may include, for example, a bowl-shaped holding member configured to hold the entire circumference of a breast as the object.

Usually, in a method called the iterative reconstruction method (the model base method), propagation, inside the object, of the photoacoustic wave generated inside the object is modeled, and a propagation simulation of the photoacoustic wave in accordance with the model is performed. Then, the optical property information inside the object, especially the initial acoustic pressure distribution is estimated such that the difference between the detection signals obtained in the simulation and the detection signals actually detected by the acoustic wave detecting elements becomes small.

Here, regarding the object information acquisition apparatus illustrated in FIG. 1, the iterative reconstruction method using an operand for which a response (e.g., reflection, refraction and absorption) of the photoacoustic wave deriving from the holding member 140 has not been considered will be described. In a propagation model of the photoacoustic wave used in the normal iterative reconstruction method, it is assumed that an acoustically homogeneous medium is used and a photoacoustic wave equation represented by Equation (1) is resolved analytically using such a medium.

[Math. 1]

$$p(r_d, t) = \frac{1}{4\pi c^2} \frac{\partial}{\partial t}\left[\frac{1}{ct}\int dr \cdot p_0(t)\delta\left(t - \frac{|r - r_d|}{c}\right)\right] \quad (1)$$

Here, $p(r_d, t)$ represents a detection signal detected at time t among the time-series detection signals obtained upon detection of the photoacoustic wave generated at a micro acoustic source located at a position r by the acoustic wave detecting element provided at a position $r_d$. c represents the acoustic velocity and $p_0(r)$ represents the initial acoustic pressure of the photoacoustic wave generated at the position r. $\delta$ is the delta function.

Since Equation (1) is linear, the photoacoustic wave equation may be expressed by Equation (2).

$$p(r_d, t) = a(r_d, r, t) \cdot p_0(r) \quad (2)$$

Here, $a(r_d, r, t)$ is an operand which represents detection, at the position $r_d$ without being externally affected, of the photoacoustic wave having the unit initial acoustic pressure generated at the position r and then conversion into a detection signal. That is, $a(r_d, r, t)$ is an operand for which the response of the photoacoustic wave by the member has not been considered.

Further, the following Equation (3) is provided if the photoacoustic wave is detected by each acoustic wave detecting element 131 and a detection signal discretized in time and space is expressed in matrix:

$$P_d = A \cdot P_0 \quad (3)$$

Here, $P_d$ is a vector which expresses, as a matrix, the time-series detection signals obtained upon detection of a photoacoustic wave affected by the member by the acoustic wave detecting elements 131. A is a vector which expresses, as a matrix, an operand for which a response of the photoacoustic wave deriving from the member has not been considered. $P_0$ is a vector which expresses, as a matrix, the initial acoustic pressure discretized in space.

For example, in the present embodiment, the number of rows of $P_d$ may be set to the number obtained by multiplying the number of the acoustic wave detecting elements by the sampling number when discretizing in time, and the number of columns may be set to 1.

The number of rows of A may be set to the number of voxels when discretizing in space, and the number of columns may be set to the number obtained by multiplying the number of the acoustic wave detecting elements by the sampling number.

The number of rows of $P_0$ may be set to the number of voxels, and the number of columns may be set to 1. That is, in this case, each matrix element of $P_0$ represents the initial acoustic pressure in each voxel.

As will be described later, using Equation (3), the matrix $P_0$ of the initial acoustic pressure may be estimated from a matrix $P_d$ of the detection signals.

However, for the matrix A of the operand of Equation (3), influences of reflection, refraction and absorption, which are caused by the member provided outside the object, of the photoacoustic wave generated inside the object have not been considered.

Therefore, if an image is reconstructed on the basis of the matrix A of an operand using, for example, the detection signal $P_d$ which has been affected by multiple reflection caused by the member provided between the object and the acoustic wave detecting elements, an artifact due to multiple reflection signals may occur in the image. The artifact may become a factor of, for example, misdiagnosis if the image is used as a diagnostic image. Therefore, it is desirable to reduce the signals that may cause such an artifact as much as possible.

The present inventor found to acquire the optical property information by performing the iterative reconstruction method using an operand for which a response deriving from the member provided outside the object has been considered (hereafter, also referred to as "operand for which the member has been considered"). Hereinafter, the iterative reconstruction method using an operand for which a response of a photoacoustic wave deriving from the member has been considered will be described.

For example, in the object information acquisition apparatus illustrated in FIG. 1, an influence upon the detection signals due to multiple reflection of the photoacoustic wave on the holding member 140 provided between the object 120 and the acoustic wave detecting elements 131 is expressed as a response signal $h_{out}$. In this case, a photoacoustic wave equation regarding a photoacoustic wave generated at the position r when the photoacoustic wave is detected by the acoustic wave detecting element 131 provided at the position $r_d$ after undergoing multiple reflection on the holding member 140 may be expressed by Equation (4) in accordance with Equation (2).

[Math. 2]

$$p_d(r_d,t) = h_{out}(r_d,r,t) \otimes a(r_d,r,t) \cdot p_0(r) \quad (4)$$

In Equation (4),

[Math. 3]

$$\otimes$$

is a convolution code (which represents a convolution operation).

Here, the response signal $h_{out}(r_d, r, t)$ and the operand $a(r_d, r, t)$ which represents the conversion into an ideal detection signal are convolved into an operand for which multiple reflection of the photoacoustic wave on the holding member 140 provided between the object 120 and the acoustic wave detecting elements 131 has been considered.

Figure 3A:
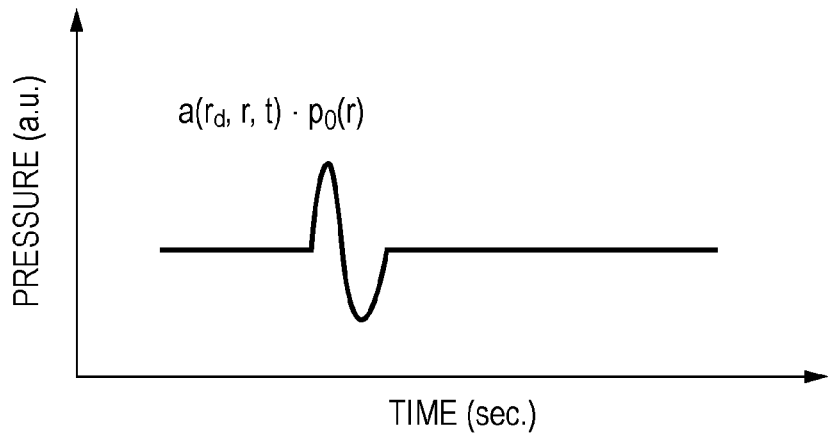
FIGS. 3A to 3C are diagrams illustrating various signals.
Figure 3B:
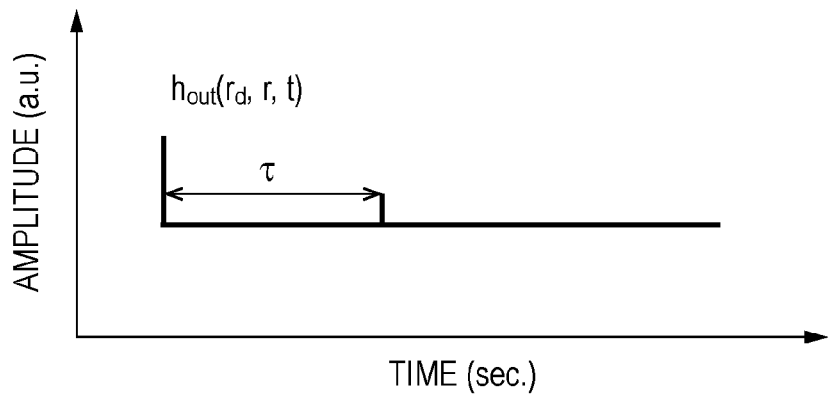
Figure 3C:
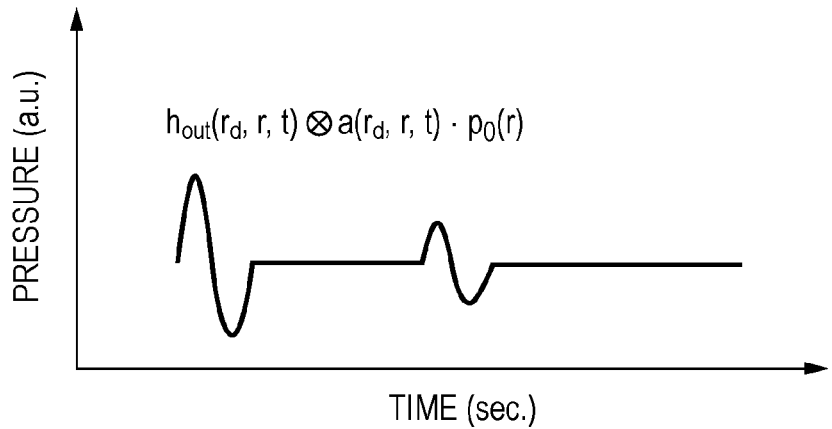

FIGS. 3A to 3C illustrate examples of various signals when the photoacoustic wave generated inside the object 120 undergoes multiple reflection within the holding member 140 provided between the object 120 and the acoustic wave detecting elements 131.

FIG. 3A illustrates an ideal detection signal $a(r_d, r, t) \cdot p_0(r)$ when a photoacoustic wave generated at a certain position r obtained by simulation is detected at the position $r_d$ without being affected by the holding member 140. The initial acoustic pressure of the photoacoustic wave generated at the position r is set to $p_0(r)$.

FIG. 3B illustrates a response signal $h_{out}(r_d, r, t)$ which represents multiple reflection of the photoacoustic wave on the holding member 140.

FIG. 3C illustrates a detection signal obtained by convolving the ideal detection signal $a(r_d, r, t) \cdot p_0(r)$ and the response signal $h_{out}(r_d, r, t)$.

Figure 4A:
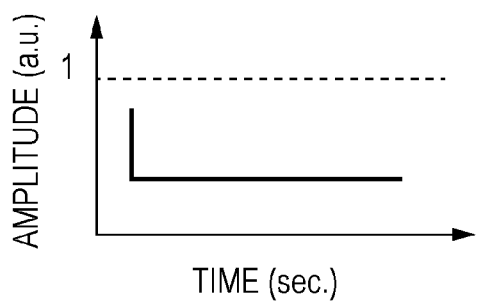
FIGS. 4A to 4D are diagrams illustrating various response signals.
Figure 4C:
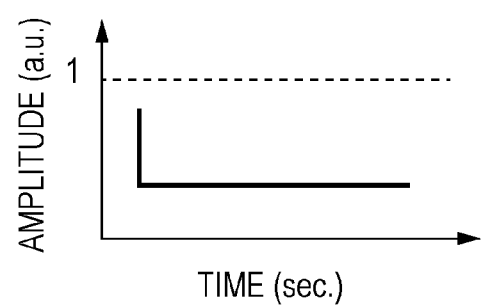
Figure 4B:
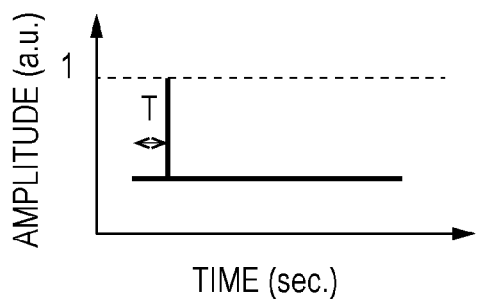
Figure 4D:
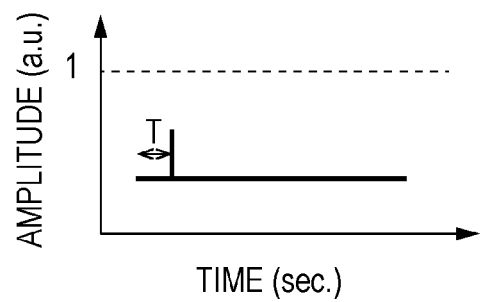

In the ideal detection signal illustrated in FIG. 3A, the photoacoustic wave is detected only once. However, in the detection signal obtained by convolving the ideal detection signal and the response signal illustrated in FIG. 3C, the photoacoustic wave will be detected twice when the multiple reflection of the photoacoustic wave on the holding member 140 is considered. Here, the cycle τ in which the response signals by the multiple reflection of the photoacoustic wave within the holding member 140 appear is determined in accordance with the position (rd) of the acoustic wave detecting element, the position (r) at which the photoacoustic wave is generated, the shape of the holding member 140, the density of the holding member 140, and the acoustic velocity of the photoacoustic wave within the holding member 140. The response by the multiple reflection is produced not only by the photoacoustic wave which enters vertically with respect to a detecting surface of a certain acoustic wave detecting element but also by the photoacoustic wave which enters obliquely with respect to the detecting surface of the certain acoustic wave detecting element. Since the photoacoustic wave which enters obliquely with respect to the detecting surface is typically a plane wave, the photoacoustic wave reflected at positions except for a position at which a certain acoustic wave detecting element exists undergoes multiple reflection within the holding member 140 and is detected by the certain acoustic wave detecting element. Therefore, the response signals corresponding to the photoacoustic wave which enters obliquely with respect to a detecting surface of a certain acoustic wave detecting element become a plurality of times of responses. The response corresponding to multiple reflection may not become a cyclic response depending on the shape of the member. FIG. 4A illustrates a response signal representing reflection of the photoacoustic wave on the holding member 140. At least a part of the photoacoustic wave is reflected on the surface of the holding member 140 and the intensity of the photoacoustic wave is decreased. Here, the intensity of the response signal which represents reflection is determined by the reflectance obtained from the acoustic impedance of the member which is determined by the density of the member and the acoustic velocity. The intensity of the response signal which represents reflection is determined by the position (rd) of the acoustic wave detecting element, the position (r) at which the photoacoustic wave is generated, and the reflection position of the photoacoustic wave obtained from the shape of the holding member 140. The intensity of the response signal which represents multiple reflection is determined by the reflectance in the same manner as in the intensity of the response signal illustrated in FIG. 4A. However, if the reflection occurs a plurality of times, it is necessary to determine the intensity from the reflectance for each reflection event. FIG. 4B illustrates a response signal which represents refraction of the photoacoustic wave on the holding member 140. The photoacoustic wave is refracted on the holding member 140 in accordance with the Snell's law and the propagation path is changed by the refraction. Therefore, as illustrated in FIG. 4B, arrival time at which the acoustic wave arrives at the acoustic wave detecting elements 131 differs by T depending on the existence of the holding member 140. Here, the difference T in the arrival time is determined in accordance with the Snell's law depending on the position (rd) of the acoustic wave detecting element, the position (r) at which the photoacoustic wave is generated, the shape of the holding member 140, the density of the holding member 140, and the acoustic velocity of the photoacoustic wave within the holding member 140. FIG. 4C illustrates a response signal which represents absorption (i.e., attenuation) of the photoacoustic wave by the holding member 140. The photoacoustic wave is absorbed by the holding member 140 and the intensity of the photoacoustic wave is decreased. Therefore, the intensity of the response signal which represents absorption is determined by an attenuation coefficient of the photoacoustic wave within the holding member 140. The intensity of the response signal which represents absorption varies also by a propagation path. That is, the intensity of the response signal which represents absorption is determined by the position (rd) of the acoustic wave detecting element, the position (r) at which the photoacoustic wave is generated, the shape of the holding member 140 and the attenuation coefficient of the holding member 140. That is, in order to determine an operand for which the member has been considered, information about the position (rd) of the acoustic wave detecting element and the position (r) at which the photoacoustic wave is generated is required. In addition to that, in order to determine an operand for which the member has been considered, at least one kind of information about the shape of the member, the density of the member, the acoustic velocity of the photoacoustic wave within the member and the attenuation coefficient of the photoacoustic wave within the member is necessary. FIG. 4D illustrates a response signal which represents refraction of the photoacoustic wave on the holding member 140 and absorption of the photoacoustic wave by the holding member 140. Here, FIG. 4D is expressed by convolution of the response signal which represents refraction of the photoacoustic wave illustrated in FIG. 4B and the response signal which represents absorption of the photoacoustic wave illustrated in FIG. 4C. That is, the response signals by a plurality of kinds of responses deriving from the member may be expressed by convolution of each response signal.

Actually, each of the acoustic wave detecting elements 131 detects photoacoustic waves generated at various positions. Therefore, if, for example, an area of interest corresponding to the object 120 is divided into N micro areas, $p_d(r_d, t)$ may be expressed by the summing of the photoacoustic waves generated at all the positions as expressed by Equation (5).

[Math. 4]

$$p_d(r_d, t) = \sum_{n=0}^{N-1} h_{out}(r_d, r_n, t) \otimes a(r_d, r_n, t) \cdot p_0(r_n) \quad (5)$$

If $h_{out}(r_d, r_n, t)$ and $a(r_d, r_n)$ are convolved into $b(r_d, r_n, t)$, Equation (6) is provided.

[Math. 5]

$$p_d(r_d, t) = \sum_{n=0}^{N-1} b(r_d, r_n, t) \cdot p_0(r_n) \quad (6)$$

If Equation (6) is expressed by a matrix, Equation (7) may be provided.

$$P_d = B \cdot P_0 \quad (7)$$

Here, B expresses, as a matrix, an operand b for which the holding member 140 provided outside the object has been considered.

Note that the operand for which the member has been considered in the present invention includes an operand for which the member has been considered which is expressed as a matrix like B.

The present invention may acquire the optical property information precisely by performing the object information acquisition method described later using such an operand for which the response of the photoacoustic wave deriving from the member has been considered.

Object Information Acquisition Method

Next, an object method of processing information performed by the signal processor 190 will be described with reference to FIG. 1. In the present embodiment, a case in which the photoacoustic wave 122 undergoes multiple reflection on the holding member 140 provided between the object 120 and the acoustic wave detecting elements 131 and then the photoacoustic wave 122 is detected by the acoustic wave detecting elements 131 will be considered. The following numbers correspond to the process numbers of FIG. 5.

Figure 5:
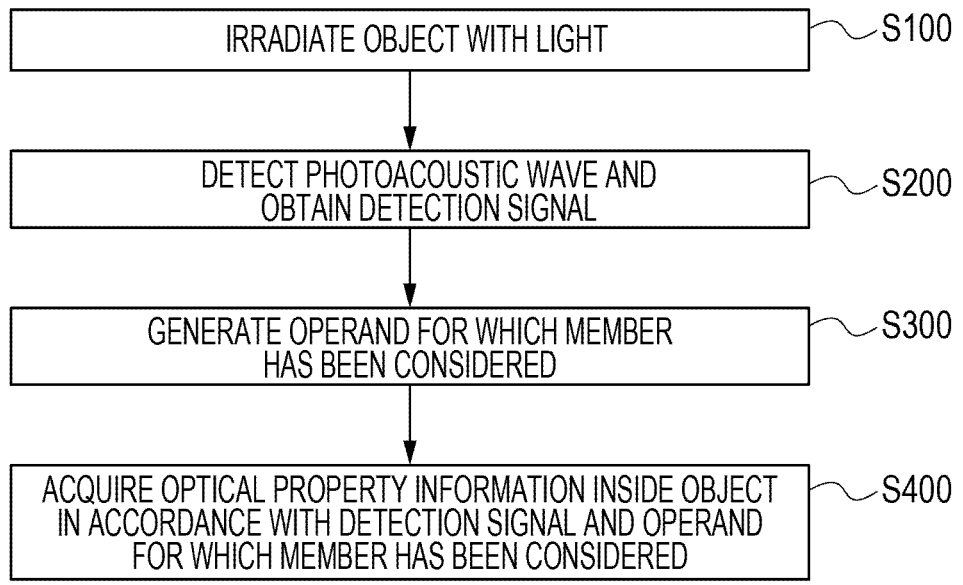
FIG. 5 is a process flow of an object information acquisition method.

First, a process flow of the object information acquisition method performed by the signal processor 190 will be described with reference to FIG. 5.

S100: Process in which Object is Irradiated with Light

In this process, the pulsed light 112 emitted from the light source 111 is guided by the optical system 113 which consists of, for example, a lens, a mirror, optical fiber and a diffuser plate while being formed into a desired light distribution shape. The pulsed light 112 illuminates the object 120. When a part of the energy of light which has propagated inside the object 120 is absorbed by the optical absorber (i.e., an acoustic source) 121, such as a blood vessel, the photoacoustic wave 122 is generated due to thermal expansion of the optical absorber 121.

S200: Process to Detect Photoacoustic Wave and Obtain Detection Signals

In this process, the acoustic wave detecting elements 131 detect the photoacoustic wave 122 which has undergone multiple reflection on the holding member 140 provided between the object 120 and the acoustic wave detecting elements 131, and output time-series detection signals. Here, the time-series detection signals are stored as the matrix $P_d$ in the storage unit 192 in the signal processing device 190.

S300: Process to Obtain Operand for which Member has been Considered

In this process, the calculating unit 191 obtains, by calculation or by experiment, an operand for which the holding member 140 has been considered used for the iterative reconstruction method. If an operand for which the member has been considered is already obtained and stored in, for example, the storage unit 192, it is not necessary to perform S300.

In order to obtain the operand for which the member has been considered, it is necessary to detect a photoacoustic wave which is generated at a micro acoustic source at an arbitrary position after the photoacoustic wave is affected by the member.

Then, there are two main methods to obtain the operand for which the member has been considered.

The first method is to obtain the operand by calculation. For example, an operand for which the member has been considered is obtained by assuming a configuration of the object information acquisition apparatus which includes the holding member 140 outside the object 120 and performing a propagation simulation of the photoacoustic wave using, for example, the FDTD for numerically analyzing a wave equation or the pseudo-spectral method. The second method is to obtain the operand by experiment. Hereinafter, these methods will be described in detail.

Figure 6:
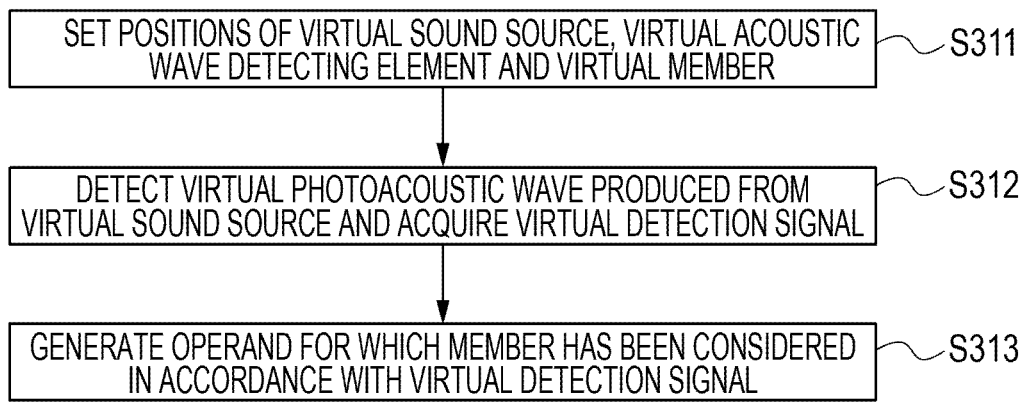
FIG. 6 is a process flow to obtain, by calculation, an operand for which a member has been considered.
Figure 7:
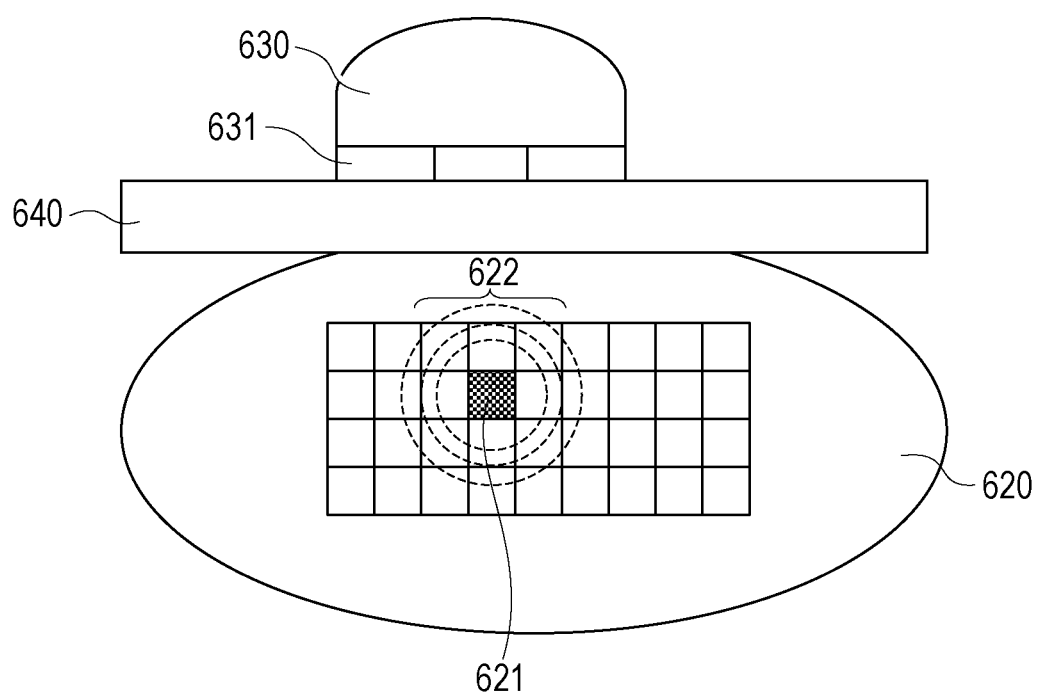
FIG. 7 is a diagram schematically illustrating a virtual object information acquisition apparatus configured to obtain, by calculation, an operand for which a member has been considered.

First, an exemplary method for obtaining, by calculation, an operand for which the member has been considered will be described with reference to FIGS. 6 and 7. FIG. 6 is a process flow to obtain, by calculation, an operand for which a member has been considered. FIG. 7 illustrates a virtual object information acquisition apparatus configured to obtain, by calculation, an operand for which a member has been considered. The following numbers correspond to the process numbers of FIG. 6. In the method by calculation, an operand for which the member has been considered is obtained from a virtual detection signal which is obtained when the calculating unit 191 performs a propagation simulation of the photoacoustic wave while setting, for example, a virtual acoustic source, a virtual acoustic wave detecting element and a virtual member.

S311: Process of Setting Positions of Virtual Sound Source, Virtual Acoustic Wave Detecting Element and Virtual Member In this process, the calculating unit 191 sets the position of a virtual acoustic source 621, the positions of a plurality of virtual acoustic wave detecting elements 631, and the position of a virtual member 640 provided outside the virtual object 620 corresponding to the object. At this time, it is desirable to set each position while considering the configuration of the object information acquisition apparatus when the photoacoustic wave is detected. In the present embodiment, the virtual member 640 is situated between the virtual object 620 and the virtual acoustic wave detecting elements 631. In the present embodiment, the virtual acoustic source 621 is set in a certain micro space when the virtual object 620 is divided into micro spaces.

Desirably, the positional relationship between the virtual acoustic wave detecting elements 631 and the virtual member 640 is set in the same manner as the positional relationship between the acoustic wave detecting elements 131 and the holding member 140. Therefore, it is desirable that a camera (e.g., a CCD) as a measuring unit obtains the positions of the acoustic wave detecting elements 131 and the position of the holding member 140 and that the calculating unit 191 sets the positions of the virtual acoustic wave detecting elements 631 and the position of the virtual member 640 in accordance with the position of each member measured by the measuring unit. Alternatively, the positions of the virtual acoustic wave detecting elements 631 and the position of the virtual member 640 may be set using the position information about the acoustic wave detecting elements 131 and the position information of the holding member 140 stored previously in the storage unit 192 of the signal processing device 190 instead of using the measuring unit.

S312: Process to Detecting Virtual Photoacoustic Wave Generated from Virtual Sound Source and to Obtain Virtual Detection Signal In this process, the virtual acoustic wave detecting elements 631 detect a virtual photoacoustic wave 622 which is generated at the virtual acoustic source 621 and obtains a virtual detection signal.

The calculating unit 191 sequentially sets the virtual acoustic source 621 to each micro space in the virtual object 620 and sequentially obtains the virtual detection signal of the virtual photoacoustic wave 622 generated at each micro space.

S313: Process to Obtain Operand for which Member has been Considered Using Virtual Detection Signal In this process, the calculating unit 191 obtains an operand for which the member has been considered in accordance with the virtual detection signal obtained in S312.

For example, the calculating unit 191 obtains a matrix B of which matrix element is each virtual detection signal corresponding to each micro area. The thus-obtained matrix B is stored in the storage unit 192 as the operand for which the member has been considered.

Figure 8:
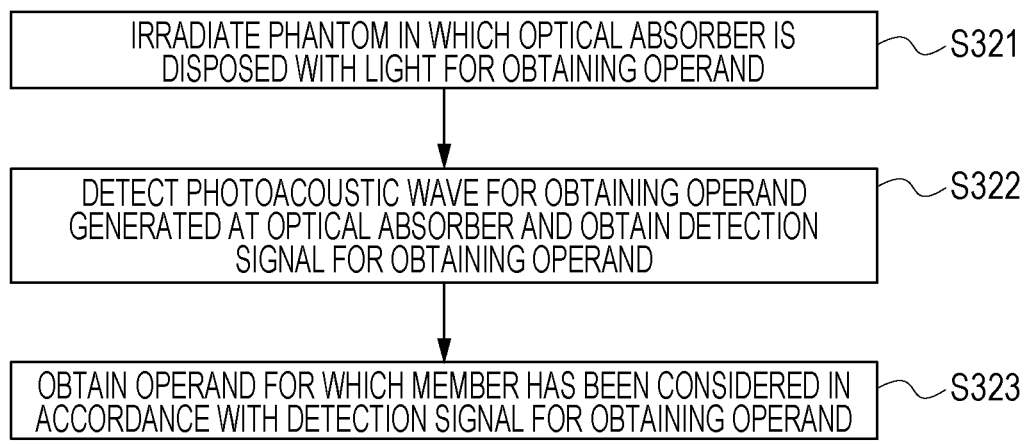
FIG. 8 is a process flow to obtain, by experiment, an operand for which a member has been considered.
Figure 9:
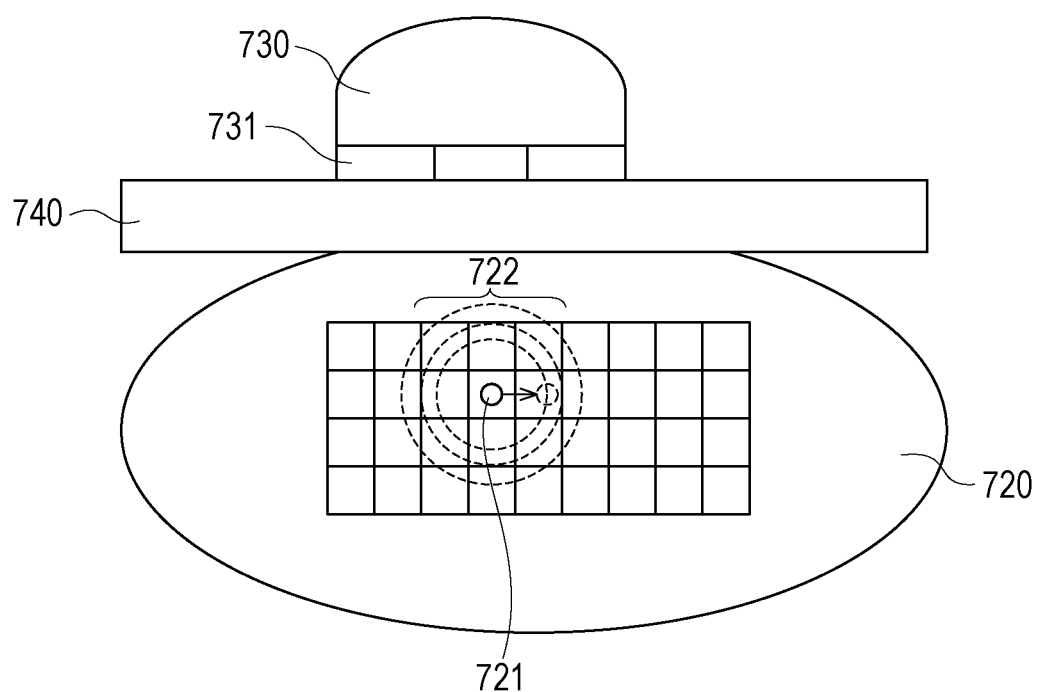
FIG. 9 is a diagram schematically illustrating an object information acquisition apparatus configured to obtain, by experiment, an operand for which a member has been considered.

Next, an exemplary method for obtaining, by experiment, an operand for which the member has been considered will be described with reference to FIGS. 8 and 9. FIG. 8 is a process flow to obtain, by experiment, an operand for which a member has been considered. FIG. 9 illustrates an object information acquisition apparatus configured to obtain, by experiment, an operand for which a member has been considered. The following numbers correspond to the process numbers of FIG. 8. In the method by experiment, an operand for which the member has been considered is obtained from a detection signal of the photoacoustic wave generated in an optical absorber 721 disposed in a phantom 720 which simulates an object.

S321: Process in which Phantom in which Optical Absorber is Disposed is Irradiated with Light for Obtaining Operand In this process, light for obtaining an operand illuminates the phantom 720 in which the optical absorber 721 is disposed. A light source which emits the light for obtaining an operand desirably has the same configuration as that of the light source 111 used in S100. The light source 111 used in S100 may be used as a light source for obtaining an operand. In the present embodiment, inside of the phantom 720 is divided into micro areas as illustrated in FIG. 9 and the light for obtaining an operand illuminates the optical absorber 721 disposed in the micro area. Then, an acoustic wave detecting element 731 detects generated photoacoustic wave 722 for obtaining an operand and outputs a detection signal for obtaining an operand.

The optical absorber 721 is sequentially disposed in each micro space in the phantom 720 and a detection signal of the photoacoustic wave for obtaining an operand generated at each micro space is sequentially obtained.

As the optical absorber 721, a colored tip which is an emitting portion of an optical fiber light source as a light source for obtaining an operand which emits light for obtaining an operand may be used. Usually, a core which is a light propagating portion of the optical fiber has a diameter of from tens to hundreds of micrometers. If the optical absorber, e.g., ink is made to adhere to the emitting portion and light is emitted through optical fiber, a photoacoustic wave is generated at the colored area and, therefore, that area may be used as a micro acoustic source. The micro acoustic source made of optical fiber is moved as illustrated in FIG. 9 and the photoacoustic wave 722 for obtaining an operand generated at each position is detected by the acoustic wave detecting element 731. Then, a detection signal for obtaining an operand is obtained. The optical fiber may be moved by a scanning mechanism which enables mechanical scanning of the optical fiber.

As the optical absorber 721, an optical absorption sheet in which, for example, optical absorbers are arranged in two dimensions may also be used. Here, the optical absorption sheet in which the optical absorbers are arranged in two dimensions is not limited to those in which the optical absorbers are arranged discretely: the optical absorption sheet may also include continuous layers of optical absorbers. To this optical absorption sheet, light is condensed to the micro area using an optical element, such as a lens, and a photoacoustic wave is generated at that light irradiation point. Thus, the micro area may be used as a micro acoustic source. By changing the light condensing point, the position of the micro acoustic source may be moved horizontally as illustrated in FIG. 9. By changing the position of the sheet vertically, the micro acoustic source may be moved also vertically. A method for moving the light irradiation point may include, for example, scanning the optical fiber which is the light source for obtaining an operand with a scanning mechanism and moving a light condensing position by an optical element, such as a lens.

Other than those methods described above, any micro acoustic source which can generate a photoacoustic wave at a plurality of positions may be used as an optical absorber.

S322: Process to Detect Photoacoustic Wave for Obtaining Operand and Obtain Detection Signal for Obtaining Operand In this process, the photoacoustic wave 722 for obtaining an operand generated when light from the light source for obtaining an operand illuminates the optical absorber 721 is detected by the acoustic wave detecting element 731 for obtaining an operand, and a detection signal for obtaining an operand is obtained. At this time, the holding member 740 for obtaining an operand is provided between the phantom 720 and the acoustic wave detecting element 731 for obtaining an operand.

Desirably, the configuration of the acoustic wave detector 730 for obtaining an operand and the configuration of the holding member 740 for obtaining an operand are the same as those of the acoustic wave detector 130 and the holding member 140 used in S200. The acoustic wave detector 130 and the holding member 140 used in S200 may be used as the acoustic wave detector 730 for obtaining an operand and the holding member 740 for obtaining an operand.

S323: Process to Obtain Operand for which Member has been Considered Using Detection Signal for Obtaining Operand In this process, the calculating unit 191 obtains an operand for which the member has been considered in accordance with the detection signal for obtaining an operand obtained in S322.

For example, the calculating unit 191 obtains a matrix B of which matrix element is each detection signal for obtaining an operand corresponding to each micro area. The thus-obtained matrix B is stored in the storage unit 192 as the operand for which the member has been considered.

In obtaining an operand by experiment described above, the photoacoustic wave 722 for obtaining an operand which is generated at the optical absorber 721 reflects all the influences of the phantom 720 which simulates the object and of the holding member 740 for obtaining an operand and is detected by the acoustic wave detecting element 731. Therefore, in the holding member 740 for obtaining an operand, an operand for which responses corresponding to all the phenomena which actually occur have been considered may be obtained. That is, if it is difficult to obtain an operand by calculation, a method by experiment is desirably used because an operand including an influence which is difficult to be assumed by calculation is obtainable.

In obtaining an operand by experiment, the measurement may take longer time if there are a large number of measurement points. In obtaining an operand by calculation, it is difficult to calculate an influence of the member precisely if the influence from the member is complicated.

Then, it is also possible to obtain an operand by combination of the method of obtaining an operand by calculation and the method of obtaining an operand by experiment.

First, for example, detection signals for obtaining an operand corresponding to several points of micro spaces are obtained in the processes of S321 and S322. Next, virtual detection signals corresponding to other micro spaces are obtained in the processes of S311 and S312. Then, the calculating unit 191 obtains an operand for which the member has been considered in accordance with the detection signals for obtaining an operand obtained by experiment and the virtual detection signals obtained by calculation.

An operand for which the member has been considered may be precisely obtained in a short time by a combination of obtaining of the detection signals for obtaining an operand by experiment and obtaining of the virtual detection signals for obtaining an operand by calculation.

S400: Process to Obtain Optical Property Information Inside Object in Accordance with Detection Signal and Operand for which Member has been Considered In this process, the calculating unit 191 of the signal processing device 190 acquires the optical property information inside the object by performing image reconstruction by the iterative reconstruction method on the basis of the detection signals obtained in S200 and the operand for which the member has been considered obtained in S300.

For example, the calculating unit 191 obtains the matrix $P_0$ of the initial acoustic pressure as the optical property information inside the object using the matrix $P_d$ of the detection signals stored in the storage unit 192 in S200 and the matrix B of the operand for which the holding member 140 has been considered stored in the storage unit 192 in S300. Here, if the matrix B of the operand is a regular matrix, the matrix B has an inverse matrix, the matrix $P_0$ of the initial acoustic pressure may be obtained from Equation (8).

$$P_0 = B^{-1} \cdot P_d \quad (8)$$

Here, $B^{-1}$ is the inverse matrix of B. As will be noted from Equation (8), the matrix $P_0$ of the initial acoustic pressure may be obtained by multiplying the inverse matrix of the matrix B of the operand for which the holding member 140 has been considered by the matrix $P_d$ of the detection signals.

Typically, however, since the matrix B of the operand may not be a regular matrix, the matrix B may not have an inverse matrix. In that case, the matrix $P_0$ of the initial acoustic pressure may be obtained, for example, by obtaining a pseudo-inverse matrix B+ of the matrix B of the operand and by using the least square method expressed by Equation (9) to obtain the matrix $P_0$ of the initial acoustic pressure which minimizes an objective function.

[Math. 6]

$$P_0 = \arg\min_{P_0} \|P_d - B \cdot P_0\|^2 \quad (9)$$

There is a possibility that the solution of Equation (9) is a localized solution and thus a true solution is not obtained. Therefore, $P_0$ which minimizes an objective function of Equation (10) to which a penalty term is added may be obtained.

[Math. 7]

$$P_0 = \arg\min_{P_0}\|P_d - B \cdot P_0\|^2 + \lambda\|P_0\|^2 \qquad (10)$$

λ is an arbitrary constant.

As described above, the matrix $P_0$ of the initial acoustic pressure may be obtained in accordance with the detection signal $P_d$ obtained by the acoustic wave detecting elements 131 and the matrix B of the operand for which the holding member 140 has been considered.

In the present embodiment, since the matrix element of $P_0$ represents the initial acoustic pressure in each voxel, it is possible to develop the initial acoustic pressure of each matrix element of $P_0$ to the initial acoustic pressure in each voxel and display the same on the display device 180 as the initial acoustic pressure distribution.

Note that the method to estimate the initial acoustic pressure distribution using the operand for which the member has been considered is not limited to those described above and various methods which have been known may be used.

The signal processing device 190 as a computer may be made to execute a program including the above-described processes.

Figure 10A:
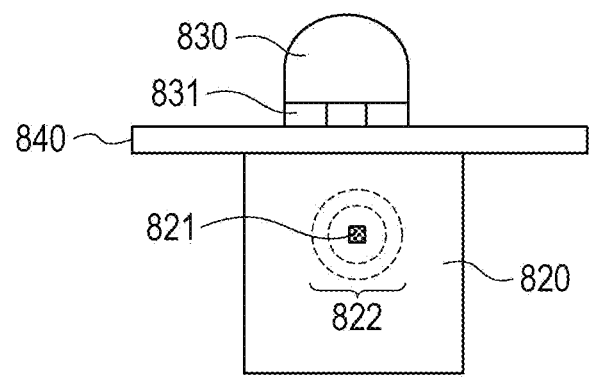
FIGS. 10A to 10D are diagrams illustrating results obtained by various image reconstruction methods.
Figure 10B:
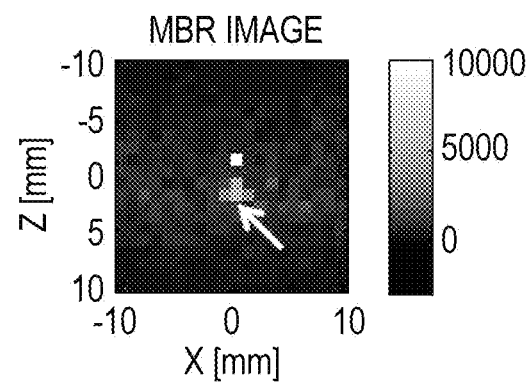
Figure 10C:
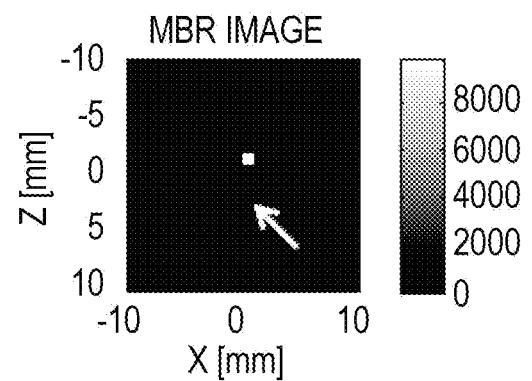
Figure 10D:
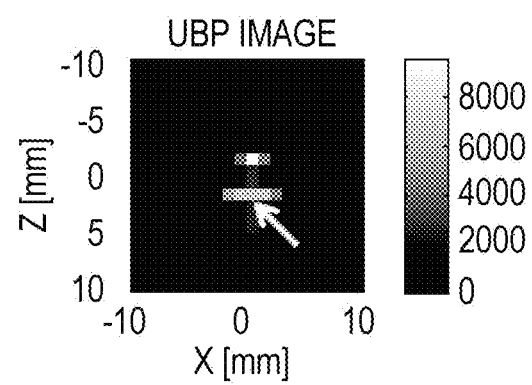

Images reconstructed by various methods are illustrated in FIGS. 10B to 10D for the comparison with the related art. FIG. 10A is a diagram illustrating a computation model of the object information acquisition apparatus used for the reconstruction.

In the object information acquisition apparatus illustrated in FIG. 10A, a holding member 840 which holds an object 820 is disposed between the object 820 and an acoustic wave detecting element 831 provided in an acoustic wave detector 830. Multiple reflection of a photoacoustic wave 822 generated in an optical absorber 821 inside the object 820 is caused by the holding member 840.

FIG. 10B illustrates initial acoustic pressure distribution $p_0$ obtained with respect to a detection signal $p_d$ detected by the acoustic wave detecting element 831 illustrated in FIG. 10A through reconstruction by the iterative reconstruction method using an operand expressed by Equation (3) for which the holding member 840 has not been considered.

FIG. 10C illustrates initial acoustic pressure distribution $p_0$ obtained through reconstruction by the iterative reconstruction method using an operand expressed by Equation (7) for which the holding member 840 has been considered.

Here, a white area represents an area where the initial acoustic pressure is high and a black area represents an area where the initial acoustic pressure is low.

In FIG. 10B, there is an area where the initial acoustic pressure is high at the position of the optical absorber 821 illustrated in FIG. 10A.

In addition, as illustrated by an arrow, there is an area where the initial acoustic pressure is high other than the position of the optical absorber 821. This area is, as described above, formed by a detection signal of the photoacoustic wave 822 which has undergone multiple reflection on the holding member 840 and not by the acoustic pressure of the optical absorber 821 actually existing in this area. Accordingly, this area is an artifact.

Also in FIG. 10C, there is an area in which the acoustic pressure is high at the position of the optical absorber 821 illustrated in FIG. 10A.

In FIG. 10C, however, the initial acoustic pressure at the position illustrated by an arrow is lower than that of FIG. 10B. This means that the artifact due to the detection signal of the photoacoustic wave which has undergone multiple reflection on the holding member 840 has been reduced.

For the comparison, initial acoustic pressure distribution obtained through image reconstruction by the back projection method is illustrated in FIG. 10D.

When FIG. 10C is compared with FIG. 10D, a large artifact occurs at the position, illustrated by an arrow, other than the position of the optical absorber 821 caused by multiple reflection on the holding member 840 in FIG. 10D.

In FIG. 10C, such an artifact caused by a detection signal due to multiple reflection is not seen. Therefore, the initial acoustic pressure distribution corresponding to the optical absorber 821 inside the object 820 is displayed more clearly in FIG. 10C than in FIG. 10D.

Thus, decreases in resolution and in quantitativity caused by the member may be reduced by performing the iterative reconstruction method in accordance with an operand for which the member provided outside the object has been considered.

Hereinafter, a main configuration of the object information acquisition apparatus according to the present embodiment will be described.

Light Source 111

The light source 111 emits light which illuminates the object and causes the object to generate a photoacoustic wave. If the object is a living body, the light source 111 desirably emits light of specific wavelength which is absorbed by a specific component among components which constitute the object. The light source 111 may be integrated with a photoacoustic imaging device of the present embodiment, or may be separated from the photoacoustic imaging device of the present embodiment.

As the light source, a pulsed light source capable of emitting pulsed light having a pulse width of the order of from several nanoseconds to several hundreds of nanoseconds as irradiation light is desirable. In particular, the pulse width about 10 nanoseconds is used to efficiently generate the photoacoustic wave. Although a laser is desirably used as the light source for its large output, other light sources, such as a light emitting diode, may also be used. Examples of the laser may include a solid-state laser, a gas laser, a fiber laser, a dye laser and a semiconductor laser. The timing of irradiation, a waveform, intensity and so forth are controlled by a light source control unit which is not illustrated.

In the present invention, if the object is a living body, the wavelength of the light source to be used is desirably selected such that light is propagated inside the object. In particular, the desirable wavelength is in a range of equal to or longer than 500 nm and equal to or shorter than 1200 nm.

Optical System 113

The pulsed light 112 emitted from the light source 111 is guided to the object by optical components, such as typically a lens and a mirror, while being formed into a desired light distribution shape. However, the pulsed light 112 may also be propagated using an optical waveguide, such as optical fiber. The optical system 113 is, for example, a mirror, a lens and a diffuser plate. The mirror reflects light. The lens condenses light, enlarges the light, and changes the shape of the light. The diffuser plate diffuses light. Any member may be used as such an optical component as long as the object 120 is irradiated with the pulsed light 112 emitted from the light source which is formed into a desired shape. Note that it is more desirable to enlarge the light to a certain amount of area than to condense using a lens from a viewpoint of safety to the object and enlargement of a diagnosing area.

A light source for obtaining an operand used to obtain an operand by experiment may be the same as the light source 111 or may be separately provided from the light source 111.

Object 120 and Optical Absorber 121

The object 120 and the optical absorber 121 will be described below although these do not constitute a part of the object information acquisition apparatus of the present invention. Main object of the object information acquisition apparatus of the present invention include diagnosis of, for example, a malignant tumor and blood vessel disease of human being and animals, and progress observation of chemical treatment. In particular, for example, a subject part of diagnosis of a breast, finger, hand and foot of a human body and an animal may be assumed as the object 120.

For example, if the object 120 is a living body, in the object information acquisition apparatus according to the present invention, a blood vessel, for example, as an optical absorber 121 existing inside the object 120 may be imaged. Examples of the optical absorber 121 may include hemoglobin, water, melanin, collagen and lipid which have a relatively larger optical absorption coefficient in the living body and body tissue consisting of these.

Acoustic Wave Detector 130

The acoustic wave detector 130 includes the acoustic wave detecting elements 131 and a housing which contains the acoustic wave detecting elements 131. The acoustic wave detecting elements 131 detect the photoacoustic wave generated by the object and convert the photoacoustic wave into an electrical signal which is an analog signal. The acoustic wave detector 130 may simply be a probe or a transducer. Any acoustic wave detector, such as a transducer using a piezoelectric phenomenon, a transducer using resonance of light and a transducer using change of capacity, may be used as long as it may detect a photoacoustic wave.

Typically, an acoustic wave detector in which the acoustic wave detecting elements 131 are arranged one-dimensionally or two-dimensionally. By using such multidimensionally arranged elements, the photoacoustic waves may be detected simultaneously at a plurality of locations. Thus, detection time may be shortened and an influence of, for example, a movement of the object may be reduced.

Signal Processing Device 190

Typically, for example, a workstation is used as the signal processing device 190. For example, an image reconstruction process is performed by software which is programmed in advance. The signal processing device 190 according to the present embodiment includes the calculating unit 191, the storage unit 192 and the control unit 193 as illustrated in FIG. 2. The calculating unit 191 typically consists of, for example, devices such as a CPU, a GPU, an amplifier, an A/D converter, a field programmable gate array (FPGA) and an ASIC. The calculating unit 191 may consist of, instead of a single device, a plurality of devices. Each process performed in the object information acquisition method according to the present embodiment may be performed by any of the devices. The storage unit 192 typically consists, for example, ROM, RAM and a medium, such as a hard disk. The storage unit 192 may consist of, instead of a single medium, a plurality of media. The control unit 193 typically consists, for example, of a device, such as a CPU. The calculating unit 191 may amplify an electrical signal output from the acoustic wave detecting element 131 and convert the electrical signal into a digital signal from an analog signal. In this description, the "detection signal" is a concept which includes both the analog signal output from the acoustic wave detecting element 131 and the digital signal which undergoes A/D conversion from the analog signal. The calculating unit 191 is desirably configured to perform a pipeline process of multiple lines of data simultaneously. With this configuration, time to acquire the object information may be shortened. The process performed in the object information acquisition method may be stored in the storage unit 192 as a program which the control unit 193 is made to perform. Note that the storage unit 192 in which the program is stored is a nontransitory recording medium, such as ROM. The signal processing device 190 and the acoustic wave detecting elements 131 may be contained in a common housing. Note that a part of signal processing may be performed in a signal processing device contained in a common housing with a plurality of acoustic wave detecting elements and the rest of the signal processing may be performed in a signal processing device provided outside the housing. In this case, the signal processing device provided inside the housing in which a plurality of acoustic wave detecting elements are contained and the signal processing device provided outside the housing may be collectively referred to as the signal processing device according to the present embodiment.

The storage unit 192 may store an operand for which a response of the photoacoustic wave deriving from the member has been considered. Since the size of the matrix of this operand is usually large, it is desirable to compress the data by setting to, for example, save only values other than zero or not to save detection signals equal to or greater than a certain detection angle in consideration of the directivity of the acoustic wave detecting elements 131. In order to reduce an operation amount in the signal processing device 190, an inverse matrix and a pseudo-inverse matrix of the matrix of the operand or only data obtained through the singular value decomposition of the matrix of the operand may be saved. It is not necessary to save the matrix of the operand itself. The storage unit 192 may independently store an operand which represents conversion into a detection signal from a photoacoustic wave when it is assumed that the photoacoustic wave is not externally affected and an operand which represents a response of a photoacoustic wave deriving from a member. According to this, the storage capacity may be made small as compared with a case in which an operand for which a response deriving from a member has been considered is stored. Especially in a case of an operand for which multiple reflection on a member has been considered, since it is necessary to keep a plurality of times of responses, a larger storage capacity is required. However, regarding a response signal h of the multiple reflection, if one-time multiple reflection is considered, for example, it is sufficient to keep two pieces of response signal data as illustrated in FIG. 3B. In addition to that, it is sufficient to keep an operand which represents conversion into a detection signal from a photoacoustic wave when it is assumed that the photoacoustic wave is not externally affected in order to obtain an operand for which a response deriving from a member has been considered. At this time, a case in which only values other than zero will be saved is considered.

Display Device 180

The display device 180 is a device which displays optical property information output from the signal processing device 190 and typically may be, for example, a liquid crystal display. The display device 180 may be provided separately from the object information acquisition apparatus of the present invention.

Member

The member is the member provided outside the object 120. As described above, the member provided outside the object may include a member provided between the object and the acoustic wave detecting elements and a member provided in the circumference of the object. In some cases, the member may desirably be optically transparent to let light penetrate the same. In that case, typically, the member may be made of plastic, such as polymethylpentene and acrylic, or glass.

A surface of the acoustic wave detecting element may also be considered as a member provided between the object and the acoustic wave detecting element. Usually, the acoustic impedance of the acoustic wave detecting element (e.g., PZT) differs from the acoustic impedance of the object. Therefore, the acoustic wave partially reflects on the surface of the acoustic wave detecting element. In order to reduce the reflection, a multilayer acoustic matching material is disposed on the surface of the acoustic wave detecting element. However, multiple reflection of the acoustic wave occurs also inside the acoustic matching material, which may cause image deterioration.

Phantom 720 which Simulates Object

As the phantom 720 which simulates the object, water contained in, for example, a tank may be simply prepared and thus desirable: however, any material may be used as long as the acoustic wave may propagate therethrough in the same manner as through the living body. It is also possible to approximate the optical constant to that of the living body by mixing Intralipid, ink and so forth.

Optical Absorber 721

As the optical absorber 721, for example, a colored tip which is an emitting portion of optical fiber or a sheet which absorbs light may be used.

For example, the material to color the tip of the optical fiber may be ink. As the material of the optical absorption sheet, a black-colored rubber sheet, an black-colored OHP sheet colored with toner, and so forth may be used.

The optical absorber 721 is prepared to provide a micro acoustic source in the phantom 720 which simulates the object, and if a sheet which absorbs light is used, it is necessary to emit light at a micro range of the sheet.

The optical absorber 721 may be any member other than those described above as long as the micro acoustic source is provided.

Other Embodiments

Embodiments of the present invention can also be realized by a computer of a system or apparatus that reads out and executes computer executable instructions recorded on a storage medium (e.g., non-transitory computer-readable storage medium) to perform the functions of one or more of the above-described embodiment of the present invention, and by a method performed by the computer of the system or apparatus by, for example, reading out and executing the computer executable instructions from the storage medium to perform the functions of one or more of the above-described embodiment. The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-091280, filed Apr. 12, 2012 which is hereby incorporated by reference herein in its entirety.

The invention claimed is:

1. An object information acquisition apparatus, comprising:
   a plurality of acoustic wave detecting elements configured to detect an photoacoustic wave generated when an object is irradiated with light and output time-series detection signals;
   a member disposed outside the object; and
   a signal processing unit configured to acquire optical property information inside the object by performing an iterative reconstruction method in accordance with the time-series detection signals and a matrix which represents reflection of the photoacoustic wave deriving from the member.

2. The object information acquisition apparatus according to claim 1, wherein the signal processing unit is configured to acquire the optical property information inside the object by performing the iterative reconstruction method in accordance with the time-series detection signals and the matrix which represents multiple reflection of the photoacoustic wave within the member.

3. The object information acquisition apparatus according to claim 1, wherein the member is disposed between the object and the plurality of acoustic wave detecting elements.

4. The object information acquisition apparatus according to claim 1, wherein the matrix is a matrix which is determined in accordance with the positions of the plurality of acoustic wave detecting elements, the position at which the photoacoustic wave is generated, a shape of the member, at least one parameter for determining the acoustic impedance of the member and an attenuation coefficient of the photoacoustic wave of the member.

5. The object information acquisition apparatus according to claim 1, wherein the signal processing unit sets virtual optical property information inside the object and acquires the optical property information by the least square method using the time-series detection signals, the matrix which represents reflection of the photoacoustic wave deriving from the member, and the virtual optical property information.

6. The object information acquisition apparatus according to claim 1, wherein the signal processing unit acquires the optical property information by multiplying the time-series detection signals expressed by a matrix by an inverse matrix of the matrix expressed as a matrix has been considered.

7. The object information acquisition apparatus according to claim 1, further comprising: a storage unit configured to store a matrix which represents conversion into a detection signal from a photoacoustic wave when it is assumed that the photoacoustic wave is not externally affected and a response signal which represents an influence upon the time-series detection signals due to reflection of a photoacoustic wave deriving from the member, wherein the signal processing unit obtains the matrix which represents reflection of the photoacoustic wave deriving from the member by convolving the matrix which represents conversion into the detection signal stored in the storage unit and the matrix which represents the influence upon the time-series detection signals due to reflection of the photoacoustic wave deriving from the member.

8. The object information acquisition apparatus according to claim 1, wherein the signal processing unit sets the position of a virtual acoustic source configured to generate a virtual photoacoustic wave, the positions of a plurality of virtual acoustic wave detecting elements configured to detect the virtual photoacoustic wave and the position of a virtual member disposed outside a virtual object which corresponds to the object and obtains the matrix which represents reflection of the photoacoustic wave deriving from the member using the virtual detection signal obtained when the plurality of virtual acoustic wave detecting elements detect the virtual photoacoustic wave.

9. The object information acquisition apparatus according to claim 8, further comprising a measuring unit configured to measure the positions of the member and the plurality of acoustic wave detecting elements, wherein the signal processing unit sets the positions of the virtual member and the plurality of virtual acoustic wave detecting elements in accordance with the positions of the member and the plurality of acoustic wave detecting elements measured by the measuring unit.

10. The object information acquisition apparatus according to claim 1, further comprising:
a phantom which simulates the object;
an optical absorber disposed inside the phantom;
a plurality of acoustic wave detecting elements for obtaining a matrix configured to detect a photoacoustic wave for obtaining a matrix generated when the optical absorber is irradiated with light for obtaining a matrix and to output a detection signal for obtaining a matrix; and
a member for obtaining a matrix disposed outside the phantom,
wherein the signal processing unit obtains a matrix which represents reflection of the photoacoustic wave deriving from the member in accordance with the detection signal for obtaining a matrix.

11. The object information acquisition apparatus according to claim 10, wherein:
the plurality of acoustic wave detecting elements and the plurality of acoustic wave detecting elements for obtaining the matrix are the same in configuration; and
the member and the member for obtaining the matrix are the same in configuration.

12. The object information acquisition apparatus according to claim 10, further comprising a light source configured to emit light for obtaining a matrix, wherein the optical absorber is disposed at an emitting portion of the light source.

13. The object information acquisition apparatus according to claim 1, further comprising:
a phantom which simulates the object;
an optical absorber disposed inside the phantom;
a plurality of acoustic wave detecting elements for obtaining a matrix configured to detect a photoacoustic wave for obtaining a matrix generated when the optical absorber is irradiated with light for obtaining a matrix and to output a detection signal for obtaining a matrix; and
a member for obtaining a matrix disposed outside the phantom,
wherein the signal processing unit sets the position of a virtual acoustic source configured to generate a virtual photoacoustic wave, the positions of a plurality of virtual acoustic wave detecting elements configured to detect the virtual photoacoustic wave and the position of a virtual member disposed outside a virtual object which corresponds to the object and obtains the matrix which represents reflection of the photoacoustic wave deriving from the member using the virtual detection signal obtained when the plurality of virtual acoustic wave detecting elements detect the virtual photoacoustic wave and the detection signal for obtaining a matrix.

14. An object information acquisition method, comprising acquiring optical property information inside the object by performing iterative reconstruction method in accordance with time-series detection signals obtained upon detection of a photoacoustic wave generated when light illuminates an object and a matrix representing reflection of a photoacoustic wave deriving from a member disposed outside the object.

15. The object information acquisition method according to claim 14, wherein, in acquiring optical property information inside the object, the optical property information inside the object is acquired by performing iterative reconstruction method in accordance with the time-series detection signals and the matrix representing multiple reflection of the photoacoustic wave within the member.

16. The object information acquisition method according to claim 14, further comprising obtaining the matrix which represents reflection of the photoacoustic wave deriving from the member by convolving a matrix which represents conversion into the detection signal stored in a storage unit and a response signal which represents an influence upon the time-series detection signals due to reflection of the photoacoustic wave deriving from the member.

17. The object information acquisition method according to claim 14, further comprising:
setting the position of a virtual acoustic source configured to generate a virtual photoacoustic wave, the positions of a plurality of virtual acoustic wave detecting elements configured to detect the virtual photoacoustic wave and the position of a virtual member disposed outside a virtual object which corresponds to the object;
detecting the virtual photoacoustic wave generated at the virtual acoustic source at the plurality of virtual acoustic wave detecting elements, and obtaining a virtual detection signal; and
obtaining the matrix which represents reflection of the photoacoustic wave deriving from the member in accordance with the virtual detection signal.

18. The object information acquisition method according to claim 14, further comprising obtaining the matrix which represents reflection of the photoacoustic wave deriving from the member in accordance with the detection signal for obtaining a matrix obtained upon detection of the photoacoustic wave for obtaining a matrix generated at the optical absorber existing inside the phantom in a state in which a member for obtaining a matrix is disposed between the phantom which simulates the object and a plurality of acoustic wave detecting elements for obtaining a matrix.

19. The object information acquisition method according to claim 14, further comprising:
setting the position of a virtual acoustic source configured to generate a virtual photoacoustic wave, the positions of a plurality of virtual acoustic wave detecting elements configured to detect the virtual photoacoustic wave, and the position of a virtual member disposed outside a virtual object which corresponds to the object;

detecting the virtual photoacoustic wave generated at the virtual acoustic source at the plurality of virtual acoustic wave detecting elements and obtaining a virtual detection signal; and obtaining the matrix which represents reflection of the photoacoustic wave deriving from the member in accordance with the detection signal for obtaining a matrix obtained upon detection of the photoacoustic wave for obtaining a matrix generated at the optical absorber existing inside the phantom in a state in which a member for obtaining a matrix is disposed between the phantom which simulates the object and a plurality of acoustic wave detecting elements for obtaining a matrix.

20. A non-transitory recording medium which stores a program for causing a computer to execute the object information acquisition method according to claim 14.

* * * * *